United States Patent [19]

Mochida et al.

[11] Patent Number: 4,479,720
[45] Date of Patent: Oct. 30, 1984

[54] APPARATUS FOR ROTATING REACTION VESSELS IN INCLINED POSTURE

[75] Inventors: Ei Mochida; Takashi Kudo, both of Tokyo; Toshiyuki Sugawara, Saitama; Minoru Tsumura, Tokyo, all of Japan

[73] Assignee: Mochida Pharmaceutical Co., Ltd., Tokyo, Japan

[21] Appl. No.: 425,251

[22] Filed: Sep. 28, 1982

[30] Foreign Application Priority Data

Oct. 8, 1981 [JP]  Japan .................. 56-160461

[51] Int. Cl.³ ................... B04B 9/10; G01N 31/00
[52] U.S. Cl. ....................... 366/214; 422/63; 422/64; 422/72; 422/102; 422/104; 436/45; 436/177; 494/16; 494/19
[58] Field of Search ............... 436/805, 807, 809, 165; 422/64, 72, 58, 63, 73; 435/300, 301, 809; 494/16, 19; 366/214

[56] References Cited

U.S. PATENT DOCUMENTS

| | | | |
|---|---|---|---|
| 3,876,379 | 4/1975 | Ghim | 436/805 |
| 3,882,716 | 5/1975 | Beiman | 422/72 |
| 3,909,201 | 9/1975 | Matte | 422/73 |
| 3,980,227 | 9/1976 | Witty et al. | 494/16 |

*Primary Examiner*—Michael Marcus
*Assistant Examiner*—Joseph P. Carrier
*Attorney, Agent, or Firm*—Parkhurst & Oliff

[57] ABSTRACT

An apparatus for rotating reaction vessels in an inclined posture, comprising a plate, means for rotatably supporting the plate, means for rotating the plate at a predetermined speed, a plurality of reaction vessel holders mounted on the edge portion of the plate and adapted for mounting reaction vessels, means for rotating the reaction vessel holders around their axes at a predetermined speed, and means for fixing the plate supporting means in such a manner that the reaction vessel holders may be inclined at a predetermined angle to the horizon.

11 Claims, 8 Drawing Figures

APPARATUS FOR ROTATING REACTION VESSELS IN INCLINED POSTURE

BACKGROUND OF THE INVENTION

The present invention relates to an apparatus for rotating reaction vessels in an inclined posture. More specifically, it relates to an apparatus adapted for use in efficiently reacting together a reactive substance bonded on a solid phase and a reactive substance in a liquid phase.

An immunological method is known which employs an antigen-antibody reaction for determining the quantity of a very small amount of substance in body fluids, or for determining the concentration of an administered medicine in blood or urine in an organism. Several methods, which are based on different principles of determination, have been known and put in practical use. They include radio-immunoassay (RIA), enzyme-immunoassay (EIA) and fluorescent-immunoassay (FIA), which have been widely employed because of their high sensitivity and their high effectiveness in quantitative determination. When these assays are carried out, the so-called sandwich method or the competitive method is generally employed as an assay method. Particularly the sandwich method is widely used, since it provides a high degree of analytical sensitivity and is easy to carry out.

According to the sandwich method, the antigen to be measured is reacted with an insolubilized corresponding antibody (first reaction), whereby an antigen-antibody complex is formed. This complex is reacted with an antibody labeled with a labeling agent and capable of combining with the antigen to be measured (labeled antibody) (second reaction). Then, the labeled antibody is divided into two portions, one having combined to the antigen-antibody complex, and another having not, and the activity of the labeling agent in either portion is measured. Similar procedures are repeated for an antigen at known concentrations to establish a calibration curve. The quantity of the antigen to be determined is obtained from the calibration curve. The labeling agent may be, for example, an enzyme, or a radioactive or fluorescent substance.

According to the competitive method, which has been first employed in radio-immunoassay, the measurement is carried out as follows:

When the antigen to be measured and a predetermined amount of the labeled antigen are reacted with the insolubilized antibody corresponding to the antigen to be measured, both antigens competitively combine with the insolubilized antibody. Next, the labeled antigen is divided into two portions, one having combined with the insolubilized antibody and another having not, and the activity of the labeling agent in either portion is measured. Similar procedures are repeated for an antigen at known concentrations to establish a calibration curve. The quantity of the antigen to be determined is obtained from the calibration curve.

In carrying out these reactions, it is advantageous to use the inner wall surface of a vessel as a carrier for a reactive substance such as an antibody to be insolubilized. For example, a plastic test tube is often used, since it serves both as a carrier for insolubilization and as a reaction vessel and it is easy to handle. The inner wall surface of a reaction vessel is, however, disadvantageous in that its surface area to which an antibody or other reactive substance is fixed is smaller than in the case of other carriers, such as plastic beads, filter paper or cellulose particles, and therefore can carry only a smaller quantity of the reactive substance. Consequently, the reaction time becomes longer according to the conventional method in which a test tube or other reaction vessel carrying an insolubilized reactive substance on its inner wall surface is kept upright and still, or its contents are stirred intermittently.

SUMMARY OF THE INVENTION

An object of the present invention is to provide an apparatus for rotating reaction vessels in an inclined posture, the apparatus being able efficiently to cause reaction between a reactive substance fixed on a solid phase and a reactive substance in a liquid phase.

In particular, the object of the present invention is to provide an apparatus for rotating reaction vessels in an inclined posture, the apparatus enabling the determination of the amount of a reactive substance in a liquid phase by a reactive substance fixed on a solid phase with improved sensitivity and in a shortened reaction time.

More specifically, the object of the present invention is to provide an apparatus for enabling measurement of an antigen or antibody in a liquid phase by an antibody or antigen or a complex of them fixed on a solid phase with improved sensitivity and in a shortened reaction time.

The apparatus according to the present invention comprises a circular plate, means for rotatably supporting the circular plate, means for rotating the circular plate at a predetermined speed, a plurality of reaction vessel holders provided on the edge portion of the circular plate, means for rotating the reaction vessel holders around their axes at a predetermined speed, and a means for fixing the whole plate in such a manner that the reaction vessel holders may be inclined at a predetermined angle to the horizon. In order to effectuate the measurement of an antigen or antibody in a liquid phase by an antibody or antigen or a complex of them fixed on a solid phase, the rotation speed of the reaction vessel holders is set at 10 to 100 rpm, preferably 25 to 55 rpm; and the angle of inclination of the reaction vessel holders is set at below 45°, preferably 10° to 20° with respect to the horizon.

These and other objects and features of the present invention will be more apparent to those skilled in the art on consideration of the accompanying drawings and following specification wherein is disclosed an exemplary embodiment of the invention with the understanding that such variations and modifications may be made therein as fall within the scope of the appended claims without departing from the spirit of the invention.

DETAILED DESCRIPTION OF THE INVENTION

The present inventors have conducted extensive study to eliminate the above disadvantages of the conventional method employing a reaction vessel as a carrier for insolubilization. As a result, they have discovered that a higher degree of sensitivity and reduction in time of reaction can be attained when the reaction vessel is inclined at a certain angle and rotated at a certain speed during reaction, instead of being kept upright and still or having its contents stirred intermittently. This discovery has led to this invention.

The present invention provides an apparatus adapted for use in a reaction wherein a reaction vessel is rotated in an inclined posture. In the following description, the reaction vessel is a test tube, the substance carried on the inner wall surface of the reaction vessel is an antibody, and the substance in the liquid phase is an antigen. This combination is, however, employed only for the convenience of description, and does not mean that this invention is limited to such a combination.

Substances in body fluids usually exist in very small quantities, and the body fluids per se containing these substances are often available only in a small volume. Any method used for measuring these substances is necessarily required to exhibit a high degree of analytical sensitivity with a sample available only in a very small quantity. Therefore, it has been usual to fix an antibody to the inner wall surface of a test tube only in the vicinity of its bottom, for example, in an area up to a height of 1 cm from the bottom of the tube.

To the contrary, the present invention enables an antibody to be fixed on a greater area including the upper portion of a test tube, since the sample, even if it is available only in a small volume, can be brought into wide contact with the antibody when the reaction vessel is rotated in an inclined posture as described herein. Moreover, the rotation of the test tube contributes to stirring its contents, and thereby enables measurement with high sensitivity in a short time.

Table 1 shows the relationship between the angle of inclination of the reaction vessel, and the relative quantity of the sample required for wetting the antibody carrying portion of the reaction vessel when the fixed area of the antibody in the vessel is constant.

Table 2 shows the relationship between the angle of inclination of the reaction vessel, and the area of contact between the sample and the inner surface of the vessel in the event the quantity of the sample is constant.

TABLE 1

| Angle of inclination | Relative volume of sample required |
|---|---|
| 90° (upright) | 1 |
| 45° | About ½ |
| 30° | About ⅓ |
| 20° | About 1/5 |
| 10° | About 1/10 |

TABLE 2

| Angle of inclination | Relative size of contact area |
|---|---|
| 90° (upright) | 1 |
| 40° | About 1.5 |
| 30° | About 2 |
| 20° | About 3 |
| 10° | About 4 |

It is generally true that the larger the contact area of two reactants, the more effectively they can be reacted. As is obvious from Table 1, the sample volume required for wetting the constant contact area decreases with a reduction in the angle of inclination of the reaction vessel toward a horizontal position. Accordingly, it is desirable to incline the reaction vessel as close as possible to the horizontal position provided that the liquid to be reacted does not flow out. Even when the inclination of the reaction vessel is very close to horizontal, for example as close as 5° above the horizon, there is no fear that the sample may fail to contact the bottom of the vessel, unless the sample volume is extremely small. Although there is no upper limit in particular to the angle of inclination of the reaction vessel, it is preferable to be kept below 45°, more preferably 10°-20°, in order to save the sample volume and raise analytical sensitivity.

It is also preferable to rotate the inclined reaction vessel at a speed of 10 to 100 rpm, more preferably 25-55 rpm. If the rotation speed exceeds 100 rpm, the sample fails to flow down along the tube wall but rotates with the vessel, whereby full contact of the sample with the antibody will deteriorate. A rotation speed lower than 10 rpm, on the contrary, causes considerable reduction of the stirring effect created by the rotation of the vessel.

Thus, an object of the present invention is to provide an apparatus adapted for use in reacting solid and liquid phases wherein a reaction vessel is kept rotating and inclined during the reaction.

The apparatus according to the present invention comprises a plate, preferably a circular plate, means for rotatably supporting the circular plate, means for rotating the circular plate at a predetermined speed, a plurality of rotatable reaction vessel holders provided on the edge portion of the circular plate, means for rotating the reaction vessel holders around their axes at a predetermined speed, and means for fixing the whole circular plate in such a manner that the reaction vessel holders may be inclined at a predetermined angle to the horizon. In order to effectuate well the measurement of an antigen or antibody in a liquid phase by an antibody or antigen or a complex of them fixed on a solid phase, the rotation speed of the reaction vessel holders is set at 10-100 rpm, preferably 25 to 55 rpm; and the angle of inclination of the reaction vessel holders is set at below 45°, preferably 10° to 20° with respect to the horizon.

The apparatus according to the present invention will now be explained in more detail with reference to the appended drawings. As a matter of course, the embodiment shown in the drawings is merely illustrative of the present invention, but it is in no way intended to limit the scope of the present invention.

Figure 1:
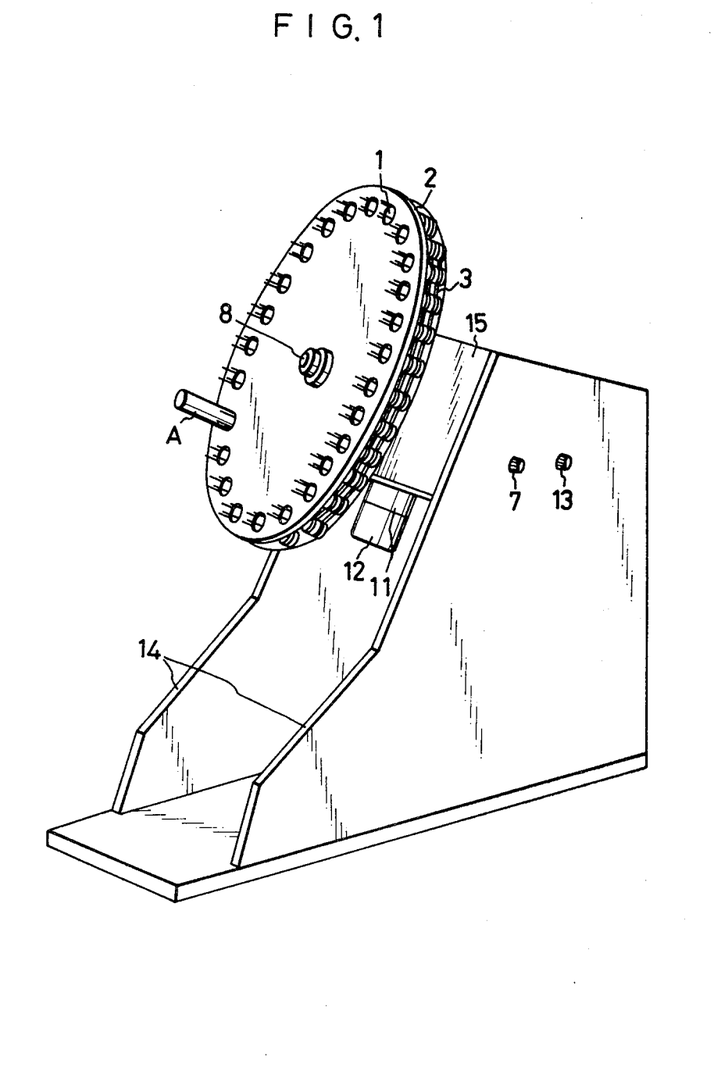
FIG. 1 is a view illustrating an apparatus according to the present invention.
Figure 2:
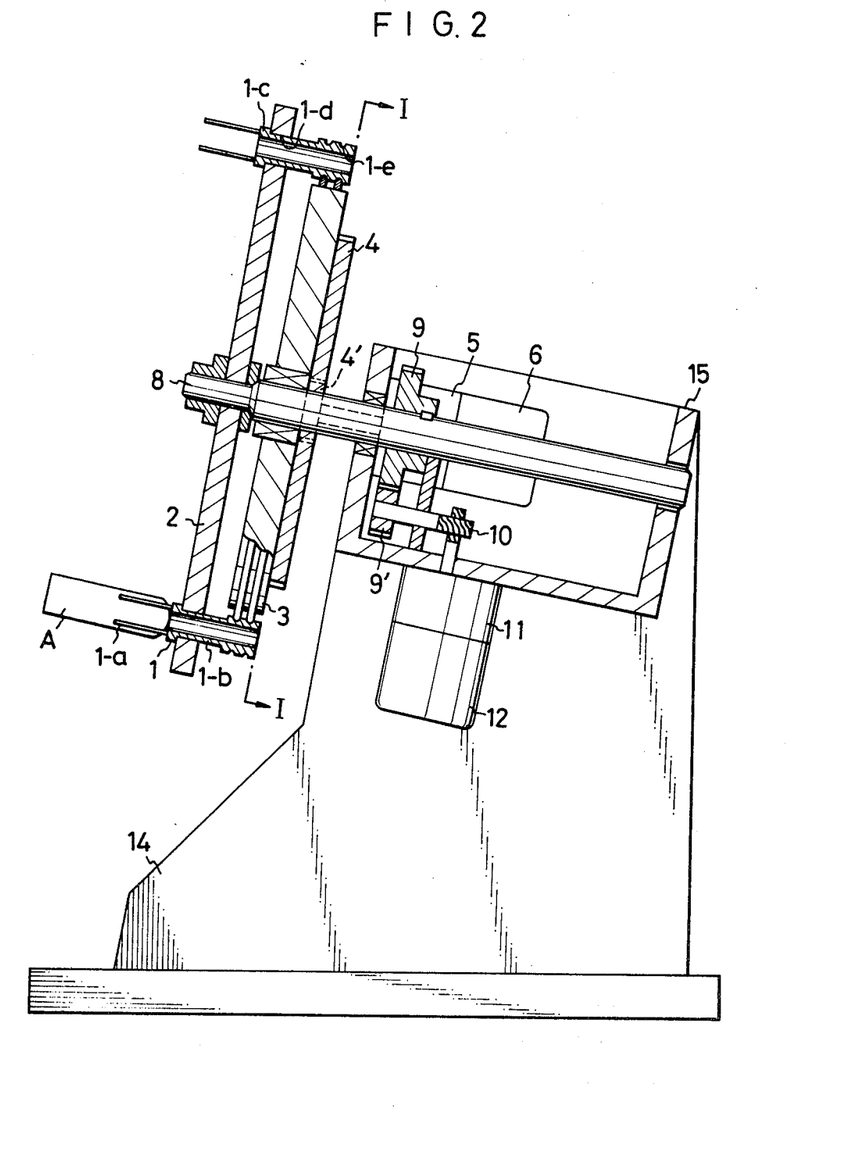
FIG. 2 is a sectional view of the apparatus illustrated in FIG. 1.

Reference numeral 2 denotes a circular plate which is rotatably supported by a rotary shaft 8. The circular shape of the plate 2 is not restrictive. Any shape of the plate will do so long as it can function as the circular plate does. At the edge portion of the circular plate 2 are provided a plurality of through-holes in preferably equally spaced relationship into which reaction vessel holders 1 are rotatably fitted. The equal spacing of the through-holes gives an excellent workability to the apparatus, but the invention is not restricted to this arrangement. The reaction vessel holder comprises two portions: a plurality of bar-like projections 1-*a* which are located over the circular plate 2 so as to hold a reaction vessel, and a cylindrical portion 1-*b* which is inserted into the through-hole of the circular plate. In FIG. 1, the number of the bar-like projections is four, but any number of projections will suffice so long as they can stably hold the reaction vessels. Further, the bar-like configuration of the projections is not indispensable. They may be in the form of an integral cylindrical wall or the like so long as they can hold the reaction vessels in such a manner that the latter rotate with the rotation of the holders. In FIGS. 1 and 2, the reaction vessel is held by the projections over the circular plate 2, but the holders may be so designed that the reaction vessel is held in the holder while a part of the holder may be under the circular plate. The cylindrical portion 1-*b* comprises a fitting portion 1-*c* which is adapted to fit the holder onto the circular plate; a sliding face 1-*d* at which the holder is rotated with respect to the through-hole of the circular plate 2; and a press-contact portion 1-*e* which is brought into contact with a rotary plate 3.

Figure 2A:
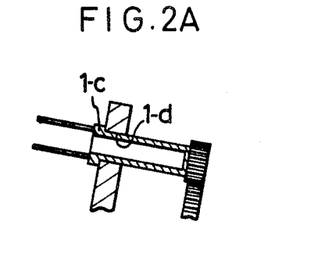
FIGS. 2A and 2B are sectional views each illustrating engaging state between a rotary plate and a holder in other embodiments according to the present invention.
Figure 2B:
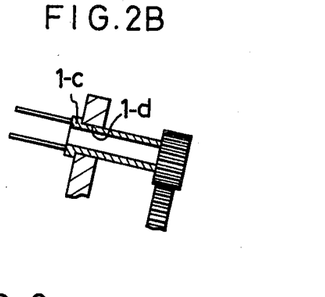

FIGS. 2A and 2B illustrate the engaging states between the holder 1 and the rotary plate 3 in other embodiments according to the present invention. In FIG. 2A, a gear is integrally attached to the bottom of the holder and engages a gear provided on the circumference of the circular plate 3. In FIG. 2B, a gear which is adapted to engage the gear provided on the circumference of the circular plate 3 is formed around the bottom portion of the holder 1.

The rotary plate 3 is fitted to and rotatably supported by the rotary shaft 8 supporting the circular plate 2. On one side of the rotary plate 3 is integrally secured a gear 4 which is adapted to engage with a gear 4' which is in turn connected to a motor 6 via a reduction gear 5, whereby the rotary motion of the motor 6 is transmitted to the holder 1 via the rotary plate 3. The rotary plate 3 is designed in a circular shape. A gear is provided on the circumference of the rotary plate in its rotary direction, while a corresponding gear is formed on the holder to engage with the gear on the rotary plate. Two circular band-like projections may be formed on the side surface of the rotary plate 3, in which case the rotary plate 3 itself need not be circular. Corresponding grooves which are adapted to engage with the projections may be formed on the side faces of the holders. The number of band-like projections of the rotary plate (grooves on the holder) is not restrictive, although it is shown as two in FIGS. 1 and 2. The band-like projections may be integrally formed with the plate portion of the rotary plate 3, or they may be formed by attaching bands onto the side face of the plate portion of the rotary plate. At least one of the contact portion 1-*e* and the band-like projections is preferably made of an elastic material so as to maintain snug contact between the holders and the rotary plate. The speed of the holder 1 is adjusted by means of an adjuster 7 such that the reaction vessels held by the holders may rotate in a range of 10 to 100 rpm. The adjuster which is adapted to control the speed of rotation of the motor 6 may be a conventional one. For instance, it may be a variable resistor which controls the current flow into the motor 6.

The circular plate 2 is secured at a tip portion of the shaft 8 and rotated by a motor 12 (separate from motor 6) via a gear 9 provided in the intermediate portion of the shaft 8, a gear 9' engaging with the gear 9, a worm gear 10 engaging with the gear 9', and a reduction gear 11 engaging with the worm gear 10, whereby the reaction vessel holders are transmitted consecutively in one circular direction. The time interval during which a reaction vessel holder in a certain location is transmitted to the location which the adjacent holder had occupied is set at an arbitrary period by means of an adjuster 13, for example, between 0.5 to 5 min.

The adjuster 13 which is adapted to control the rotation speed of the circular plate 2 may be a conventional one. For instance, it may be a timer which controls the motor 12. Control by means of the adjusters 7 and 13 may be achieved electrically or electronically. As a matter of course, such adjusters may be omitted in the fixed state type apparatus in which the rotation speeds of the holders 1 and the circular plate 2 are fixed preliminarily at constant speeds.

Figure 3:
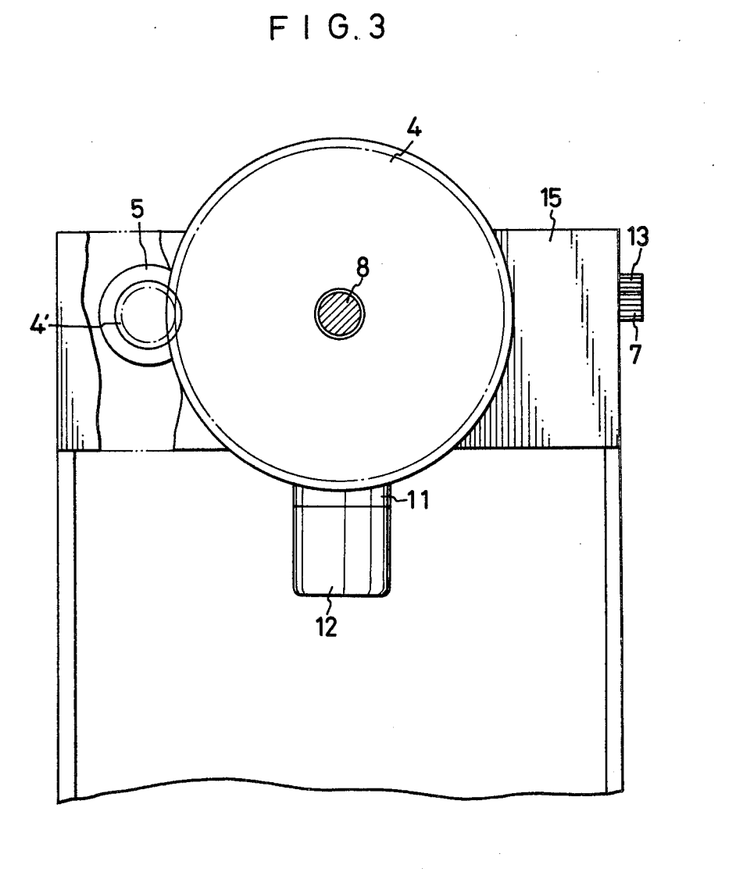
FIG. 3 is a partially sectional view of the apparatus as cut along line I—I in FIG. 2.

The above parts are supported by an appropriate supporting means such as box 15 shown in FIGS. 1-3.

The above-mentioned apparatus is supported by supporting plates 14 when in use. The supporting plates 14 are designed such that the reaction vessels held by the holders 1 may be inclined at 0° to 90° upwardly from horizon. In the embodiment shown in the drawings, inclining means is the supporting plates 14, but it may be adjustable means (not shown) which enables the reaction vessel to be inclined to the horizon at an arbitrary angle. For instance, the adjustable means may be so constituted that the box-like supporting means 15 is, adjustably in inclined angle, supported on the supporting plates 14 by means of a screw or the like. The supporting means 14 serves to support the parts 1-13 and the box-like supporting means 15. The plates 14 are not restricted to a specific profile as shown in FIGS. 1 and 2.

Further, in the embodiment as shown in the drawings, the box-like supporting means 15 is separately formed from the supporting plates 14 and secured to the plates 14 by an appropriate means such as an adhesive agent or bolts. But the supporting means 15 and the supporting plates 14 may be integrally formed.

In the embodiments as specifically described above, two motors 6 and 12 are provided to rotate the circular plate 2 and the holder 1 respectively. But, as a matter of course, only one motor is sufficient to drive the circular plate and the rotary plate when appropriate power transmission means is employed.

The reaction method of this invention has the following advantages:

(i) Continuous rotation of the reaction vessel ensures sufficient stirring of the reaction mixture, improved reaction efficiency, and high sensitivity and improved accuracy of the assay.

(ii) In order to obtain an assay system of high sensitivity, it has hitheto been usual to employ an increased volume of sample. According to this invention, however, it is sufficient to use a sample volume which is equal to only $\frac{1}{2}$ to 1/10 of that which has hitherto been required, as shown in Table 1. This has the same effect as if the conventional method has been carried out with a sample volume of twice to ten times as much as that usually employed.

Figure 4:
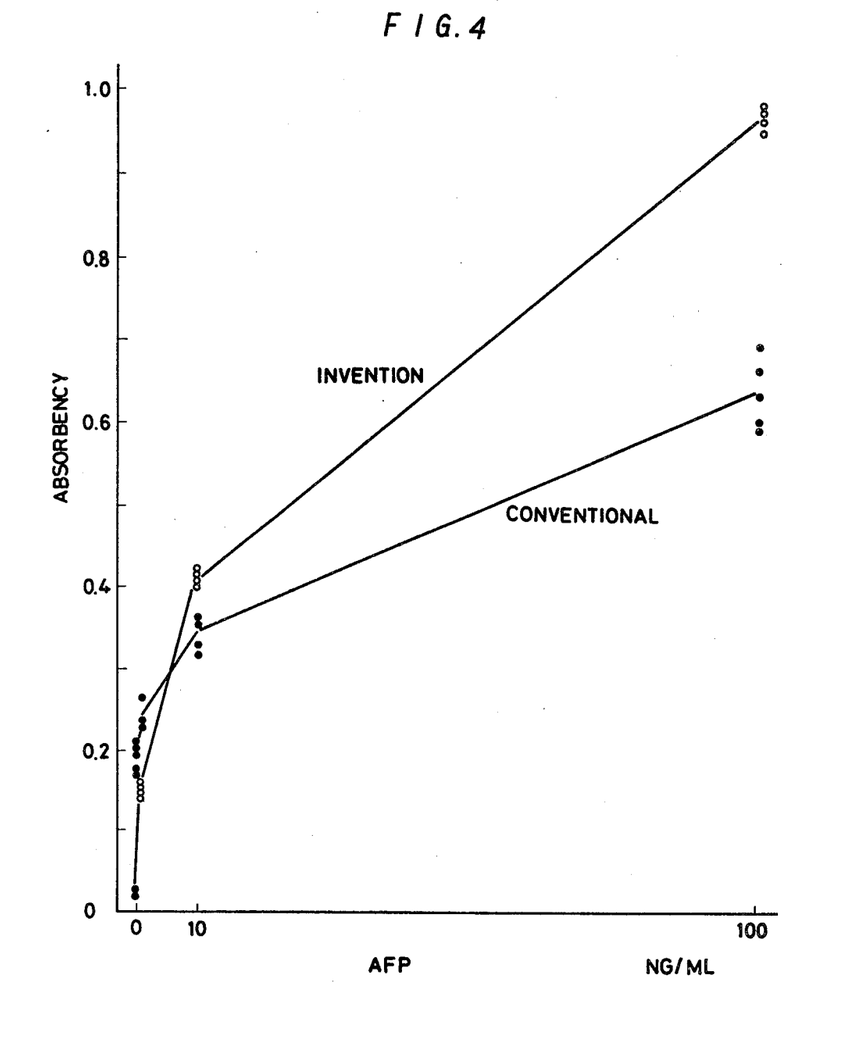
FIG. 4 is a graph in which the calibration curve obtained employing the apparatus according to the present invention is compared with that obtained by conventional apparatus.

(iii) In the conventional method, when the volume of sample is small, the gradient of the calibration curve becomes lower, reducing the accuracy of measurements obtained by this method. When the apparatus according to this invention is employed, however, the contact area between the sample and the inner surface of the reaction vessel can be increased to 1.5 to 4 times that which has hitherto been obtained, even if the same small volume of sample is employed, as shown in Table 2. As the antibody can be bound to the enlarged area, it is possible to obtain an assay system of high sensitivity and accuracy. Table 3 shows the results of an assay for alpha-fetoprotein (ASP) performed by using the same reagent and the same sample volume. Tests were repeated five times at each concentration employing the apparatus of this invention and a conventional one. FIG. 4 shows calibration curves based on the results shown in Table 3. It is noted that the calibration curve according to this invention has a higher gradient than that of the conventional method, and that the apparatus of this invention therefore provides higher accuracy. These assays for AFP according to the present invention were performed in a reaction vessel inclined at an angle of 10°, and rotated at a speed of 30 rpm.

TABLE 3

| AFP concentration (ng/ml) | 0 | 1 | 10 | 100 |
|---|---|---|---|---|
| Conventional method | | | | |
| Optical (X ± SE) density | 0.193 ± 0.007 | 0.240 ± 0.007 | 0.346 ± 0.009 | 0.639 ± 0.019 |
| CV % | 8.5 | 6.2 | 6.0 | 6.7 |
| Method of this invention | | | | |
| Optical (X ± SE) density | 0.025 ± 0.001 | 0.154 ± 0.002 | 0.412 ± 0.105 | 0.970 ± 0.006 |
| CV % | | 7.4 | 2.4 | 2.6 | 1.3 |

Figure 5:
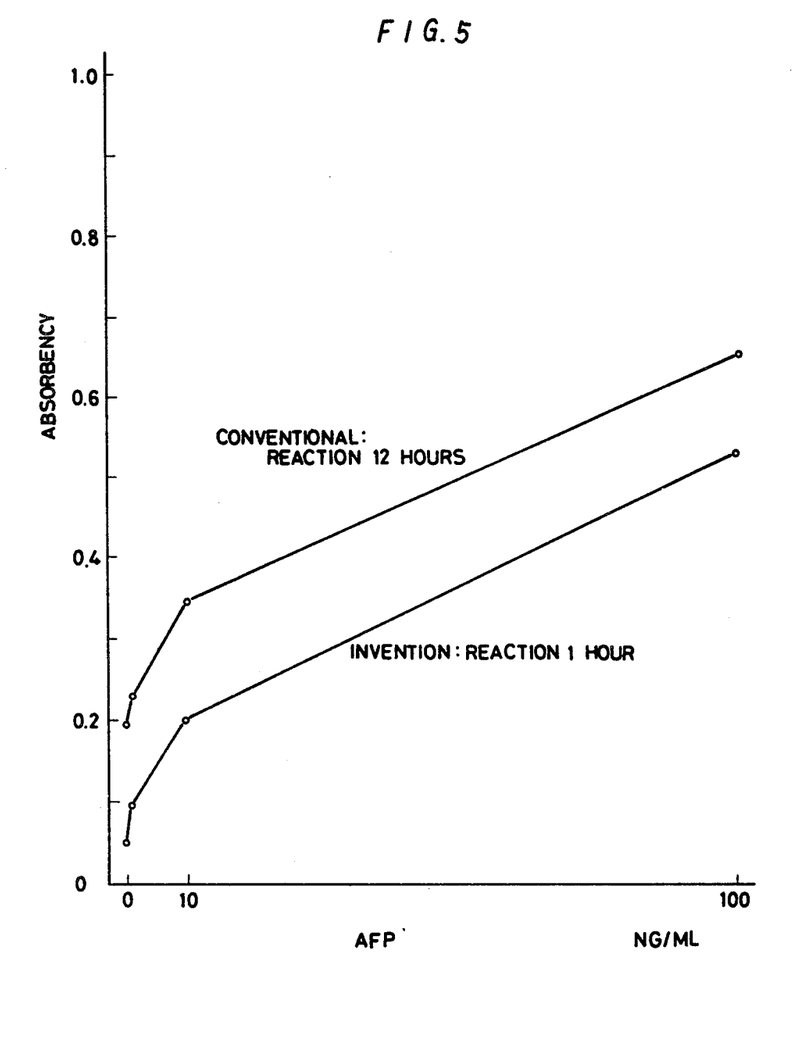
FIG. 5 is a graph showing that the apparatus according to the present invention enables the reaction time to be shortened.

(iv) The reaction time can be greatly reduced. For example, Table 4 shows by comparison assay times required for obtaining similar analytical sensitivities and accuracies, i.e., calibration curves having similar gradients, by using the same reagent in an assay for AFP. It was found that the apparatus according to the present invention enables 1 hr. measurement, thereby reducing the reaction time to a large extent. The reaction vessel was inclined at an angle of 20°, while it was rotated at a speed of 50 rpm. The standard curves thus obtained are shown in FIG. 5. It is noted that the reduction in assay time was so great that the reactions which had required a total of 12 hours according to the conventional method could be accomplished in one hour according to the apparatus of this invention.

TABLE 4

| | Conventional method (Vessel is kept upright and still) | Method of this invention (Vessel is inclined and rotated) |
|---|---|---|
| First reaction | 60 min. | 20 min. |
| Second reaction | 60 min. | 20 min. |
| Enzyme reaction | 10 hours | 20 min. |

The apparatus may be used for transferring the reaction vessels one after another automatically, while they are rotated continuously and their contents are stirred continuously. Accordingly, it is, for example, possible to mount a multiplicity of reaction vessels each containing a sample liquid one after another on the reaction vessel holders at the starting position, cause the reaction to be completed in the reaction vessels while they are rotated and transferred forward automatically, and examine the results of the reaction in a predetermined position automatically by, for example, a spectrophotometer. Thus, the apparatus of this invention is particularly suitable for automation of the assay system. It is apparent that changes may be made to the exemplary apparatus described herein without departing from the scope of the invention as claimed below.

The reaction method of this invention will now be described with reference to an example.

EXAMPLE 1

Assay For AFP (a) Preparation of Reaction Test Tubes 2 ml of monoclonal anti-AFP antibody [A] (1 mg/ml) was placed in each polystyrene test tube which had been washed with 0.05 M phosphorous acid physiological saline buffer solution (pH 6.4) (hereinafter referred to as PBS). Incubation was performed at 56° C. for 20 minutes to give a test tube sensitized with the antibody [A]. A second monoclonal antibody [B] of a clone different from that of [A] was labeled with horse-radish peroxidase (Boehringer Manheim Grade I, which will hereinafter be referred to simply as HRPO) by the method of Nakane et al., described in J. Histochem. Cytochem., 22, 1084 (1974). The second antibody was diluted with PBS to one fiftieth, and 1 ml of the diluted antibody was placed in each polystyrene test tube sensitized with antibody [A]. After the test tubes had been lyophilized they were tightly closed to provide reaction vessels for AFP assay.

(b) Assay for AFP

Test tubes for AFP assay prepared as described at (a) above were charged with 0.9 ml of PBS. In each test tube was placed 0.1 ml of standard AFP solution prepared by diluting AFP with normal human serum to contain 1, 10, 100 or 1,000 ng of AFP per milliliter. The test tubes were mounted on the holders in the apparatus according to the present invention while inclined upwardly at an angle of 20° to the horizon. The reaction was carried out for 30 minutes, while the test tubes were rotated at a speed of 50 rpm. After the reaction, the test tubes were washed with physiological saline solution containing 0.005% of Tween 20 (hereinafter referred to as washing agent). Each test tube was then charged with 2 ml of an enzyme substrate solution containing 50 ng/ml of 5-amino-salicylic acid and 0.01% of hydrogen peroxide. The test tubes were again mounted on the holders while inclined upwardly at an angle of 20° to the horizon, and the reaction was carried out for 30 minutes, while the test tubes were rotated at a speed of 50 rpm.

Figure 6:
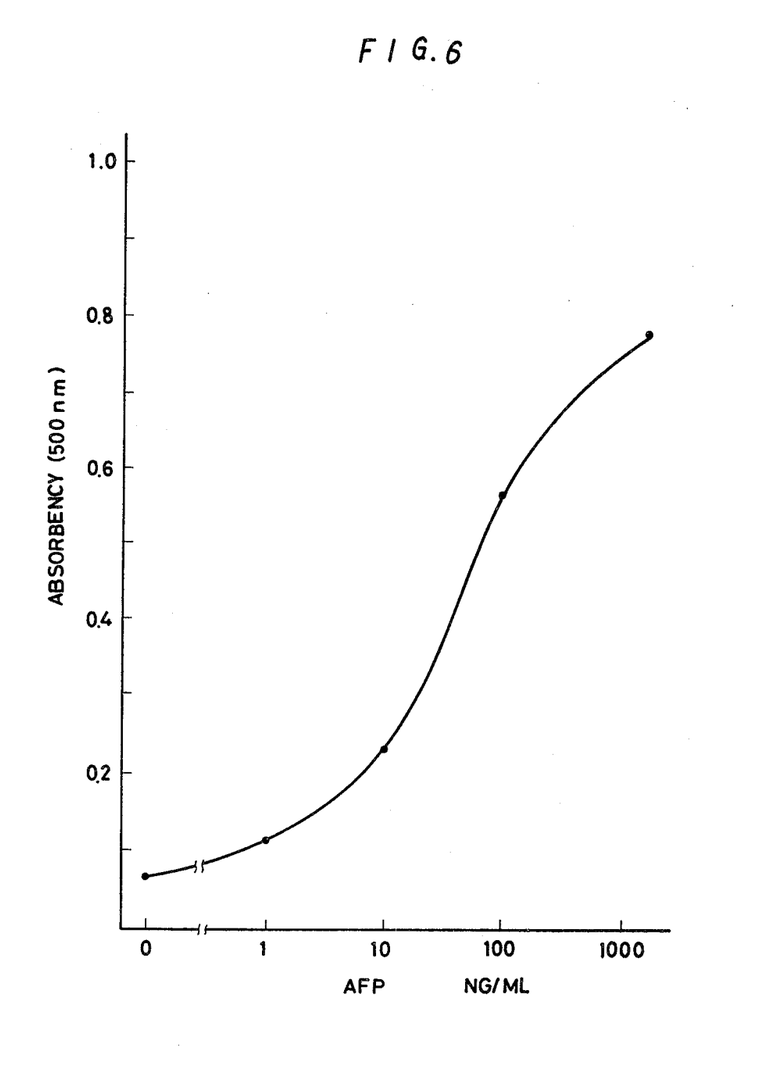
FIG. 6 is a graph showing a calibration curve for AFP assay in Example 1.

Then, 50 μl of 2% sodium azide was added to terminate the reaction. The absorbency of the reaction mixture was examined at a wavelength of 500 nm by a spectrophotometer. The calibration curve obtained therefrom is shown in FIG. 6.

What is claimed is:

1. An apparatus for rotating a plurality of reaction vessels in an inclined posture, comprising:
    a first plate fastened on a shaft inclined to a horizontal plane and rotatable by a first driving means;
    a plurality of vessel holders disposed on a concentric circular line on said first plate and held rotatably thereon with their axes of rotation parallel to said shaft;
    a second plate supported rotatably on said shaft and rotatable by a second driving means at a speed independent of the speed of rotation of said first plate, said second plate being associated with said first plate in such a manner that rotation of said second plate causes rotation of said vessel holders about their said axes of rotation and a base fixing the shaft in such a manner that the reaction vessel holders may be inclined at an angle to the horizontal plane.

2. The apparatus for rotating reaction vessels in an inclined posture according to claim 1, wherein said first and second plates are circular, said first and second driving means each comprises a motor and a gear train, and an outer periphery of said second circular plate contacts outer peripheries of said vessel holders whereby rotation of said second circular plate causes rotation of said vessel holders.

3. The apparatus for rotating reaction vessels in an inclined posture according to claim 1, wherein an angle of inclination of said shaft is adjustable.

4. The apparatus for rotating reaction vessels in an inclined posture according to claim 1, wherein said driving means is adapted to rotate said reaction vessel holders at 10 to 100 rpm.

5. The apparatus for rotating reaction vessels in an inclined posture according to claim 4, wherein said second driving means is adapted to rotate said reaction vessel holders at 25 to 55 rpm.

6. The apparatus for rotating reaction vessels in an inclined posture according to claim 1, 4 or 5, wherein the shaft is inclined at an angle of below 45° with respect to the horizontal plane.

7. The apparatus for rotating reaction vessels in an inclined posture according to claim 6, wherein the shaft is inclined at an angle of 10° to 20° with respect to the horizontal plane.

8. The apparatus for rotating reaction vessels in an inclined posture according to claim 1, wherein the reaction vessel holder comprises a first portion for holding a reaction vessel, a second portion for slidably fitting the reaction vessel holder to the first plate, and a third portion which is brought into contact with said second plate, said first and third portion being located on opposite sides of the first plate respectively.

9. The apparatus for rotating reaction vessels in an inclined posture according to claim 1 or 8, further comprising an adjuster for controlling the rotation speed of the reaction vessel holders.

10. The apparatus for rotating reaction vessels in an inclined posture according to claim 9, further comprising an adjuster for controlling the rotation speed of the first plate.

11. An apparatus for rotating reaction vessels in an inclined posture comprising:
    a first plate;
    a shaft for rotatably supporting said first plate, said shaft being rotated by a first electric motor via a reduction gear at a predetermined speed;
    a plurality of holes provided on an edge portion of the first plate in an equally spaced relationship;
    a plurality of reaction vessel holders fitted into the holes, said reaction vessel holders having a first portion located over the first plate so as to hold a reaction vessel, a fitting portion adapted to fit the reaction vessel holder through the hole, and a contact portion is located under the first plate;
    a second plate which is rotatably supported by the shaft, one side face of which is provided with a first gear which is adapted to engage with a corresponding second gear provided on the side face of the contact portion of each reaction vessel holder;
    a third gear secured to the rear face of the second plate, said second plate being rotated by means of a second motor via a reduction gear, a fourth gear engaging with the third gear and the reduction gear, and the third gear for rotating the reaction vessel holders via the second plate at a predetermined speed; and
    a base fixing the shaft in such a manner that the reaction vessel holders may be inclined at a predetermined angle to a horizontal plane.

* * * * *